United States Patent [19]

Carlin et al.

[11] Patent Number: 4,657,007

[45] Date of Patent: Apr. 14, 1987

[54] NEBULIZER

[75] Inventors: Benson Carlin, Princeton, N.J.; Edward H. Ransom, Ashland, Va.

[73] Assignee: Whittaker General Medical Corporation, Richmond, Va.

[21] Appl. No.: 392,490

[22] Filed: Jun. 28, 1982

[51] Int. Cl.[4] ............................................ A61M 11/00

[52] U.S. Cl. ........................... 128/200.18; 128/200.21

[58] Field of Search .................. 128/200.14, 200.18 X, 128/200.21 X, 200.23

[56] References Cited

U.S. PATENT DOCUMENTS

| | | | |
|---|---|---|---|
| 3,658,059 | 4/1972 | Steil | 128/200.21 |
| 3,838,686 | 10/1974 | Szetely | 128/200.18 |
| 4,054,622 | 10/1977 | Lester | 128/200.18 X |
| 4,116,387 | 9/1978 | Kremer et al. | 128/200.18 X |
| 4,251,033 | 2/1981 | Rich et al. | 128/200.21 X |
| 4,333,450 | 6/1982 | Lester | 128/200.18 X |

*Primary Examiner*—Edward M. Coven
*Attorney, Agent, or Firm*—Donald E. Nist

[57] ABSTRACT

An improved nebulizer is provided which includes a hollow generally elongated housing defining a central chamber containing a body of nebulizable liquid. The housing has a gas entry port adjacent its lower end and a nebulized liquid exit port adjacent its upper end. A gas conduit having a central passageway is connected to and extends below the gas entry port and includes a branch which extends laterally thereof and defines a gas relief port. The relief port may have a removable cap and is used to control the flow of gas into the chamber (by means of blocking the relief port or leaving the relief port open). Thus, fingertip control of the flow of nebulized liquid from the nebulizer is provided. An elongated nozzle assembly is connected to the gas entry port and extends up in the chamber. The assembly includes an inner gas-containing tube connected to the gas conduit and an outer annular liquid-containing tube having access to the body of nebulizable liquid. The upper ends of the tubes are flat, contain small exit orifices and are spaced to provide a contact area for the gas and liquid. The outer tube's upper end has a removable cap containing a central rounded target aligned with the orifices so as to break up into fine droplets a gas and liquid mixture exiting the orifices. A diffuser is disposed between the target and the exit port. The housing may comprise upper and lower sections releasably secured together and the diffuser, conduit and nozzle assembly may be integral with the housing. The nebulizer is inexpensive and durable.

6 Claims, 3 Drawing Figures

NEBULIZER

BACKGROUND OF THE INVENTION

1. Field of the Invention

The present invention generally relates to liquid droplet—forming means and, more particularly, to an improved finger-controlled nebulizer.

2. Prior Art

Various types of nebulizers have been provided to break up liquid into fine droplet form for dispensing for medical purposes. Most of the earlier types of nebulizers were of the fly spray configuration, with a stream of liquid intersecting a stream of gas at about a right angle. More recently, more effective nebulizers have employed coaxial liquid and gas conduits terminating in mixing chambers. Some have employed some form of target against which the gas-liquid mixture can be directed to break up the droplets into a desired small size. However, most such nebulizers have been found to be complicated, expensive, difficult to clean and operate and otherwise unsatisfactory. Frequently, the medication dispensed in droplet form from the nebulizer is expensive and all of the medication must be used to provide the proper dosage to the patient for inhalation purposes. For one reason or another, it is frequently necessary to temporarily suspend operation of the nebulizer. This usually results in a significant loss of medication in the form of nebulized droplets exiting the nebulizer but not into the patient. In many instances, it is also difficult for the patient to control the rate of delivery of the nebulized medication and to shut the nebulizer off.

Although one nebulizer has been devised to allow the patient to regulate the flow of nebulized liquid from the nebulizer by closing or opening a side port near the main exit port or keeping it partially open or closed by finger control, unfortunately this device permits the loss of nebulized liquid from the side port.

Accordingly, there remains a need for a simple, inexpensive, durable efficient nebulizer which can be easily filled, cleaned and re-used. The nebulizer should include means which will permit the flow rate of nebulized material from the exit port to be easily controlled by the patient utilizing the nebulizer. This control means should not result in any substantial loss of medication either in nebulized or unnebulized form from the nebulizer.

SUMMARY OF INVENTION

All the foregoing needs have now been satisfied by the improved nebulizer of the present invention. The nebulizer is substantially as set forth in the Abstract above. Thus, the nebulizer includes a gas inlet conduit which has a branch which operates as a gas relief port and is easily controlled by the patient. Thus, the patient can block the gas relief port partially or fully so as to effect partial or full flow of nebulized material from the nebulizer. If the gas relief port is left wide open, gas flow is substantially totally diverted from the nebulizer so that flow of nebulized material from the nebulizer stops. A cap may be provided over the exit port and can be left in place when the nebulizer is to be used at full flow rate. By placing the fingertip control relief port upstream of the nebulizing portion of the device, nebulized material is not lost when it is desired to reduce the flow rate or stop it completely, in contrast to conventional devices.

The nebulizer includes an elongated nozzle assembly employing a pair of coaxial inner and outer tubes supplying gas and liquid to a mixing area between the top of the inner tube and the top of the outer tube. Exit orifices extend through the flat tops of the inner and outer tubes and direct the liquid-gas mixture into contact with a rounded target coaxially aligned therewith and fixed in a porous cap releasably disposed on the top of the outer tube. The spacing between the target and top surface of the outer tube can be controlled to vary the nebulizing effect of the target. The diffuser, conduit and nozzle assembly may be integral with the housing. Various other features of the present invention are set forth in the following detailed description and accompanying drawings.

DRAWINGS

DETAILED DESCRIPTION

FIGS. 1 & 3

Figure 1:
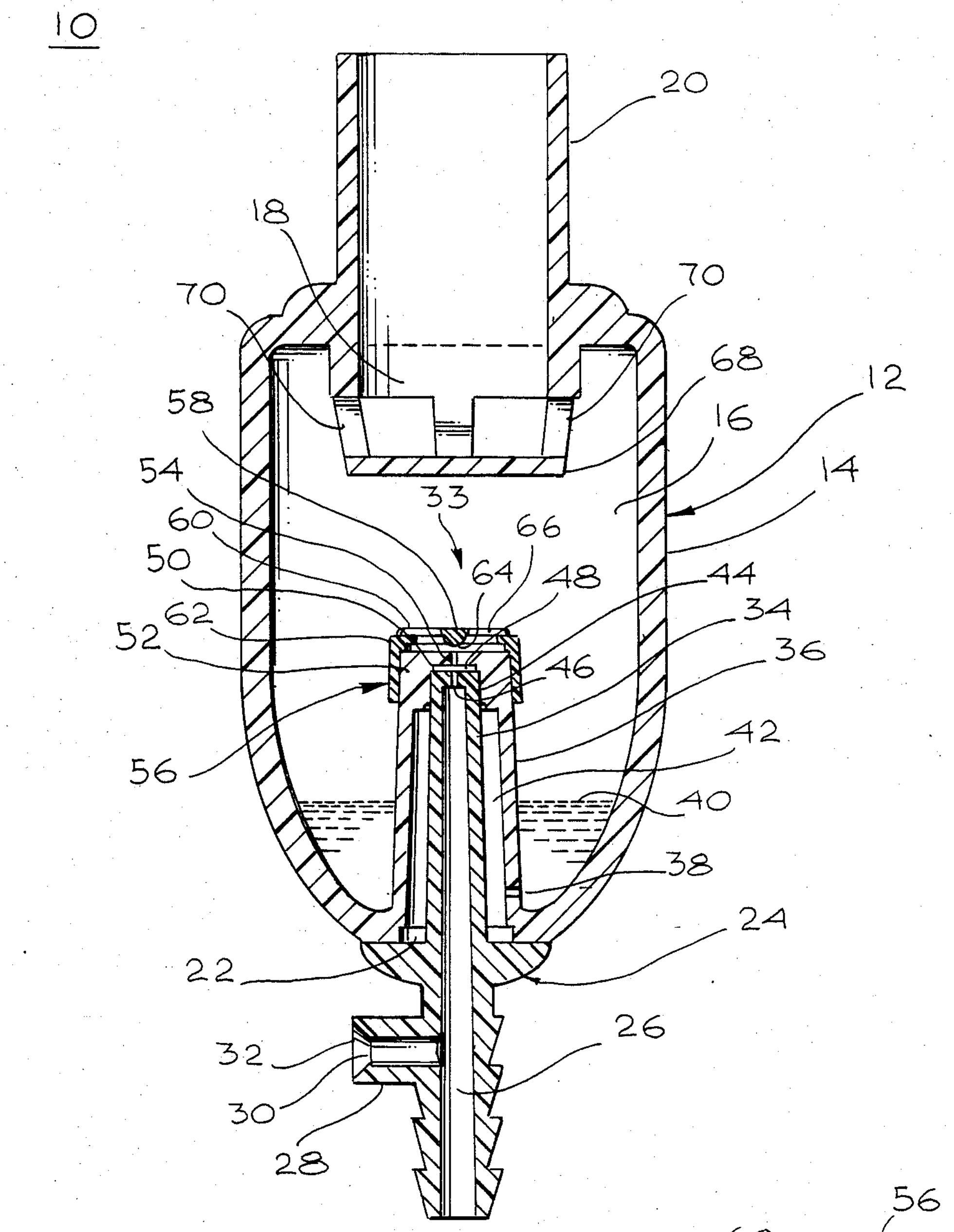
FIG. 1 is a schematic cross-section of a first preferred embodiment of the improved nebulizer of the present invention.

Now, referring more particularly to FIG. 1 of the accompanying drawings, a first preferred embodiment of the improved nebulizer of the present invention is schematically depicted in cross section therein. Thus, nebulizer 10 is shown which comprises a body or casing 12 of preferably transparent self-supporting material such as plastic, glass or the like. Casing 12 includes a main elongated central portion 14, preferably bell-shaped or generally cylindrical and defining a hollow central chamber 16. The upper end of chamber 16 has a nebulized material exit port 18 to which is integrally connected an upstanding cylindrical funnel 20 dimensioned for insertion into the mouth of a patient to deliver nebulized material to the lungs of the patient.

The lower end of chamber 16 has an entry port 22 within which is fitted in sealing engagement therewith a gas entry conduit 24. Conduit 24 forms part of casing 12 and has a central gas passageway 26 extending upwardly therethrough. Conduit 24 also includes a branch 28 having a central passageway 30 intersecting passageway 26, as shown in FIG. 1. When gas relief port 32, that is, the outer end of passageway 30 is left open, gas passing through passageway 26 is diverted into passageway 30 and out of exit port 32 to a sufficient extent to prevent nebulization of liquid in nebulizer 10. Port 32 can be closed partially or fully by a patient utilizing nebulizer 10, merely by placing a finger over port 32. Thus, the patient can control the rate of flow of nebulized liquid from funnel 20.

A nozzle assembly 33 is disposed in an upstanding position in chamber 16 and includes in the embodiment shown in FIG. 1 the upper portion 34 of conduit 24 and an outer annular tube 36 coaxial with and spaced outwardly of portion 34. Tube 36 has a transverse passageway 38 which communicates with a body 40 of nebulizable liquid disposed in the lower end of chamber 16 below the top of tube 36. Passageway 38 also communicates with an elongated space 42 defined between tube 36 and portion 34.

The upper end 44 of portion 34 is flat and defines a vertical central orifice 46 communicating with passageway 26 and a disc-shaped space 48 between the lower flat surface 50 of the upper end 52 of tube 36 and end 44. Space 48 communicates with passageway 42 (not shown) and serves as a mixing chamber for gas passing up through passageway 26 and for liquid passing up through passageway 42 into space 48. A vertical orifice 54 is coaxial with orifice 46 and extends up through the flat upper end 52 of tube 36.

Figure 3:
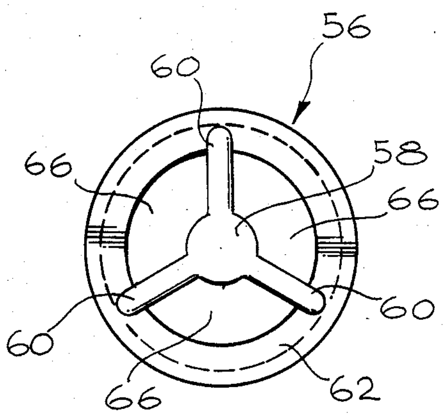

A removable cap 56 is disposed above end 52, rests on end 52 and slip fits down over the side of end 52, as FIG. 1. Referring particularly to FIGS. 1 and 3, cap 56 is cylindrical in top plan view and includes a central target 58 supported by radiating spokes 60 integral with rim 62 of cap 56. The lower end 64 of target 58 is curved and is coaxial with orifice 54 but spaced above orifice 54 a pre-determined distance. A gas-liquid mixture exiting upwardly through orifice 54 impinges on end 64, is broken up into a fine mist or spray and is deflected upwardly through openings 66 in cap 56, but cannot immediately exit chamber 16 into funnel 20, due to the presence of a diffuser plate 68 supported below and in line with funnel 20 by a plurality of spaced legs 70. Nebulized liquid migrates upwardly around plate 68 and into and out of funnel 20 for direct delivery to the patient.

During the passage of air or other gas up through passageway 26, a partial vacuum is created in passageway 42 so that liquid medication from body 40 is sucked through passageway 38 and up into and out of passageway 42 during operation of the nebulizer. The rate of flow of gas through passageway 26 is as, previously indicated, controlled by the patient by blocking port 32 partially or fully with the thumb or one of the fingers while holding a nebulizer 10 in the hand.

Nebulizer 10 can be easily fabricated of polystyrene or other suitable plastic or of glass by casting, moulding or the like and preferably is in transparent form. Cap 56 can be made to fit snugly enough on end 52 so that the spacing between end 64 and orifice 54 can be regulated to control the droplet size of the nebulized material. Nebulizer 10 offers a very durable highly efficient configuration which is light in weight, easy to use and of very low cost.

FIG. 2

Figure 2:
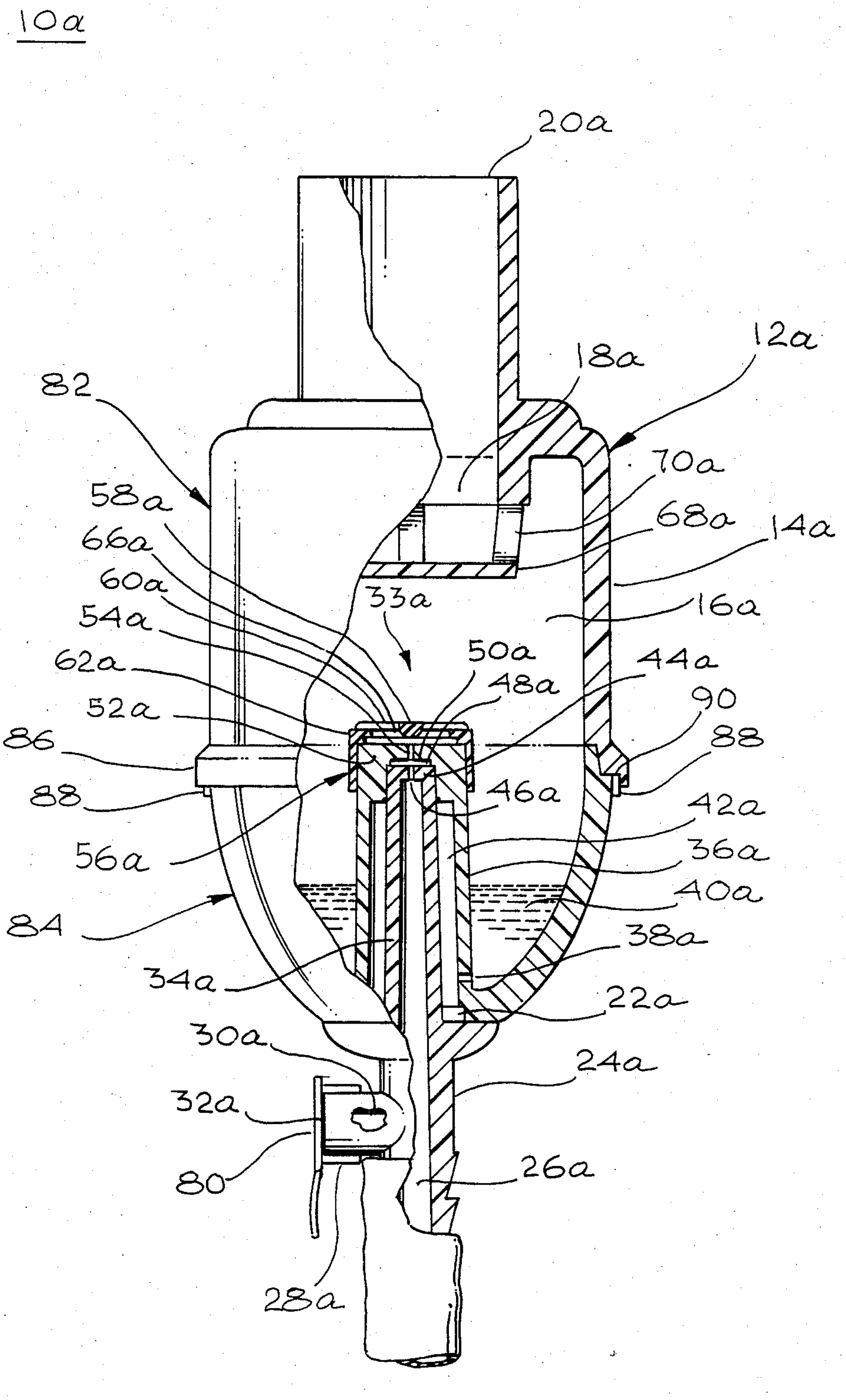
FIG. 2 is a schematic front elevation, partly broken away, of a second preferred embodiment of the nebulizer of the present invention, showing the nebulizer connected to an air hose and bearing a removable cap on the gas relief port; and, FIG. 3 is a schematic top plan view of the target-bearing cap of FIG. 1.

A second preferred embodiment of the improved nebulizer of the present invention is schematically depicted in FIG. 2. Thus, nebulizer **10*a* is shown. Components of nebulizer 10*a* which are similar to those of nebulizer 10 bear the same numerals but are succeeded by the letter "a". Thus, nebulizer 10*a* includes casing 12*a* with central portion 14*a* defining chamber 16*a* having exit port 18*a* to which funnel 20*a* is connected. Entry port 22*a* receives conduit 24*a* which has gas passageway 26*a* and a side branch 28*a* containing passageway 30*a* and gas relief port 32*a*. Relief port 32*a* is covered by a removable cap 80 of plastic, rubber or the like. Cap 80 permits nebulizer 10*a* to be utilized in the full flow mode without having to keep a thumb or finger over port 32*a***.

A body of liquid **40*a* to be nebulized is disposed in the lower end of chamber 16*a* below the upper end of nozzle assembly 33*a*, which comprises a gas-containing upper end 44*a* of conduit 24*a* surrounded by an outer tube 36*a*. Passageway 38*a* communicates between liquid 40*a* and passageway 42*a*. The remainder of the nozzle assembly is also substantially identical to that previously described for nebulizer 10 and includes cap 56*a* with target 58*a* in line with orifice 54*a*. A diffuser plate 68*a* is also provided and is integral with casing 12*a***.

Casing **12*a* is formed of two interlocking sections 82 and 84 which releasably join together at the flanged lower end 86 of section 82, as shown in FIG. 2. Thus, the upper end of section 84 is provided with outwardly projecting detents 88 which interlock with and are received within grooves 90 in flanged portion 88. Thus, section 82 can be unscrewed from and left off of section 84 to clean chamber 16*a*, adjust the position of cap 56*a*, etc. This arrangement increases the utility and reuseability of nebulizer 10*a*. Nebulizer 10*a* can be fabricated of materials similar to those of nebulizer 10 and otherwise has the advantages of nebulizer 10**.

Various modifications, changes, alterations, and additions can be made in the embodiments of the nebulizer of the present invention, and in the components and parameters thereof. All such modifications, changes, alterations, and additions as are within the scope of the appended claims form part of the present invention.

What is claimed is:

1. An improved nebulizer, said nebulizer comprising in combination:

A. A hollow generally elongated housing defining a central chamber containing a body of nebulizable liquid, said housing including a gas entry port adjacent the lower end thereof and a nebulized liquid exit port adjacent the upper end thereof;

B. a gas conduit having a central passageway connected to said gas entry port and extending below paid chamber, said gas conduit including a branch extending generally laterally of said conduit and defining a gas relief port;

C. seal means releasably sealing said gas relief port;

D. an elongated nozzle assembly connected to said gas entry port and extending up into said chamber, said assembly including an inner gas-containing tube coaxial with said gas conduit, an outer annular liquid-containing tube disposed around and over said gas-containing tube and defining a lateral passageway extending to said liquid body, the upper ends of said two tubes being flat and containing coaxial exit orifices of reduced size, the liquid of said outer tube contacting the gas of said inner tube below the upper end of said outer tube and a removable perforated cap adjustably slideably received over said outer tube and bearing a target spaced above and in line with said orifices, whereby a gas and liquid mixture exiting said orifices and impinging on said target is broken up into small adjustably sized droplets; and, E. a diffuser disposed within said chamber adjacent said exit port to prevent direct flow of nebulized liquid out of said port.

2. The improved nebulizer of claim 1 wherein said housing comprises upper and lower sections releasably secured together.

3. The improved nebulizer of claim 2 wherein said sections interconnect in a generally horizontal plane at about the level of said cap.

4. The improved nebulizer of claim 1 wherein said diffuser, conduit and nozzle assembly are integral with said housing.

5. The improved nebulizer of claim 1 wherein said cap comprises a depending annular peripheral rim and a horizontal portion secured to the upper end of said rim and including said target disposed in a central depending position, and spokes secured to and radiating from said target to said rim.

6. The improved nebulizer of claim 1 wherein the lower end of said target is curved to deflect said liquid and gas mixture and is closely spaced from the flat top surface of the upper end of said outer tube, wherein the upper end of said outer tube has a flat bottom surface and wherein said inner and outer tubes are dimensioned to provide a flat disc shaped contact space for said gas and liquid between the flat top surface of the upper end of such inner tube and the flat bottom surface of the upper end of said outer tube.

* * * * *